US010155713B2

(12) United States Patent
Richter et al.

(10) Patent No.: US 10,155,713 B2
(45) Date of Patent: Dec. 18, 2018

(54) CATALYST ARRANGEMENT WITH OPTIMIZED VOID FRACTION FOR THE PRODUCTION OF PHTHALIC ACID ANHYDRIDE

(71) Applicant: Clariant International Ltd., Muttenz (CH)

(72) Inventors: Oliver Richter, Germering (DE); Gerhard Mestl, München (DE); David Lesser, München (DE); Robert Marx, München (DE); Nadine Fromm, Grosskarolinenfeld (DE); Felix Schulz, München (DE); Peter Schinke, München (DE); Werner Pitschi, Bruckmühl (DE)

(73) Assignee: Clariant International Ltd. (CH)

( * ) Notice: Subject to any disclaimer, the term of this patent is extended or adjusted under 35 U.S.C. 154(b) by 0 days.

(21) Appl. No.: 14/900,831

(22) PCT Filed: Apr. 23, 2015

(86) PCT No.: PCT/EP2015/058849
§ 371 (c)(1),
(2) Date: Dec. 22, 2015

(87) PCT Pub. No.: WO2015/162227
PCT Pub. Date: Oct. 29, 2015

(65) Prior Publication Data
US 2017/0320803 A1   Nov. 9, 2017

(30) Foreign Application Priority Data
Apr. 24, 2014  (DE) .................. 10 2014 005 940

(51) Int. Cl.
| C07C 51/265 | (2006.01) |
| C07D 307/89 | (2006.01) |
| B01J 8/06 | (2006.01) |
| B01J 23/22 | (2006.01) |
| C01G 31/02 | (2006.01) |
| C07D 307/83 | (2006.01) |

(52) U.S. Cl.
CPC ............. C07C 51/265 (2013.01); B01J 8/067 (2013.01); B01J 23/22 (2013.01); C01G 31/02 (2013.01); C07D 307/89 (2013.01); B01J 2208/00044 (2013.01); B01J 2208/00513 (2013.01); B01J 2208/025 (2013.01); B01J 2208/065 (2013.01); C07D 307/83 (2013.01)

(58) Field of Classification Search
CPC ........ C07C 51/265; B01J 23/22; C01G 31/02; C07D 307/83
See application file for complete search history.

(56) References Cited

U.S. PATENT DOCUMENTS

| 5,723,658 A | 3/1998 | Pfirmann et al. |
| 5,792,719 A | 8/1998 | Eberle et al. |
| 6,362,345 B1 | 3/2002 | Heidemann et al. |
| 6,369,240 B1 * | 4/2002 | Hara ............... B01J 23/002 549/248 |
| 6,380,399 B1 | 4/2002 | Okuno et al. |
| 6,700,000 B1 | 3/2004 | Heidemann et al. |
| 7,390,911 B2 | 6/2008 | Neto et al. |
| 7,592,293 B2 | 9/2009 | Guckel et al. |
| 7,615,513 B2 * | 11/2009 | Guckel ............. B01J 23/002 502/350 |
| 7,618,918 B2 | 11/2009 | Estenfelder et al. |
| 7,968,491 B2 | 6/2011 | Guckel et al. |
| 7,985,705 B2 | 7/2011 | Storch et al. |
| 8,097,558 B2 | 1/2012 | Estenfelder et al. |
| 8,263,789 B2 * | 9/2012 | Wilmer ............ B01J 8/0496 549/248 |
| 8,796,173 B2 | 8/2014 | Wolk et al. |
| 9,067,187 B2 | 6/2015 | Wilmer et al. |
| 2008/0064593 A1 | 3/2008 | Guckel et al. |
| 2009/0312562 A1 | 12/2009 | Guckel et al. |
| 2017/0044125 A1 | 2/2017 | Richter et al. |

FOREIGN PATENT DOCUMENTS

| CN | 1280979 | 1/2001 |
| CN | 1795049 | 6/2006 |
| CN | 101090769 | 12/2007 |
| CN | 101232944 | 7/2008 |

(Continued)

OTHER PUBLICATIONS

PCT international Search Report for PCT/EP2015/058849, dated Jul. 15, 2015.
PCT International Preliminary Report on Patentability for PCT/EP2015/058849, dated Oct. 25, 2016.
Machine English Translation of DE 10 2008 011 011, Aug. 6, 2009.
Machine English Translation of JP 2010-149105 Jul. 8, 2010.
Machine English Translation of JP 2001-064274, Mar. 13, 2001.
Machine English Translation of JPS 61-221149, Oct. 1, 1986.
State Intellectual Property Office of The People's Republic of China Search Report for Chinese Application No. 201580001204.X, dated Oct. 8, 2016.

(Continued)

Primary Examiner — Anthony J Zimmer

(57) ABSTRACT

The invention relates to a catalyst arrangement for preparing phthalic anhydride by gas-phase oxidation of aromatic hydrocarbons, which comprises a reactor having a gas inlet end for a feed gas and a gas outlet end for a product gas and also a first catalyst zone made up of catalyst bodies and at least one second catalyst zone made up of catalyst bodies, where the first catalyst zone is arranged at the gas inlet end and the second catalyst zone is arranged downstream of the first catalyst zone in the gas flow direction and the length of the first catalyst zone in the gas flow direction is less than the length of the second catalyst zone in the gas flow direction, characterized in that the first catalyst zone has a higher gap content compared to the second catalyst zone.

15 Claims, No Drawings

(56) References Cited

FOREIGN PATENT DOCUMENTS

| | | |
|---|---|---|
| DE | 10 2008 011 011 | 8/2009 |
| EP | 0 037 492 | 10/1981 |
| EP | 0 744 214 | 11/1996 |
| EP | 0 985 648 | 3/2000 |
| EP | 1 526 123 | 4/2005 |
| EP | 2 363 203 | 9/2011 |
| JP | S 61-221149 | 10/1986 |
| JP | 2001-064274 | 3/2001 |
| JP | 2002-516319 | 6/2002 |
| JP | 3490684 | 1/2004 |
| JP | 2008-531633 | 8/2008 |
| JP | 2010-149105 | 7/2010 |
| KR | 2000-0052776 | 8/2000 |
| WO | WO 93/01155 | 1/1993 |
| WO | WO 99/61433 | 12/1999 |
| WO | WO 99/61434 | 12/1999 |
| WO | WO 2004/103944 | 12/2004 |
| WO | WO 2006/092304 | 9/2006 |
| WO | WO 2007/134849 | 11/2007 |
| WO | WO 2008/077791 | 7/2008 |
| WO | WO 2011/032658 | 3/2011 |

OTHER PUBLICATIONS

English Translation of State Intellectual Property Office of The People's Republic of China Notification of the First Office Action for Chinese Application No. 201580001204.X, dated Oct. 17, 2016.
English Translation of Korean Patent Office Notice of Preliminary Rejection for Korean Patent Application No. 10-2016-7027882, dated Sep. 20, 2017.

* cited by examiner

CATALYST ARRANGEMENT WITH OPTIMIZED VOID FRACTION FOR THE PRODUCTION OF PHTHALIC ACID ANHYDRIDE

The invention relates to a catalyst arrangement for preparing phthalic anhydride by gas-phase oxidation of aromatic hydrocarbons, which comprises a reactor having a gas inlet end for a feed gas and a gas outlet end for a product gas and also a first catalyst zone made up of catalyst bodies and at least one second catalyst zone made up of catalyst bodies, where the first catalyst zone is arranged at the gas inlet end and the second catalyst zone is arranged downstream of the first catalyst zone in the gas flow direction and the length of the first catalyst zone in the gas flow direction is less than the length of the second catalyst zone in the gas flow direction, characterized in that the first catalyst zone has a higher gap content compared to the second catalyst zone.

The industrial production of phthalic anhydride is carried out by catalytic gas-phase oxidation of ortho-xylene and/or naphthalene. For this purpose, a catalyst suitable for the reaction, generally a vanadium-containing catalyst, is provided in a reactor and a reaction gas is passed over the catalyst. A shell and tube reactor in which a plurality of tubes are arranged in parallel and a coolant flows around them is preferably used as reactor. As coolant, use is generally made of a salt melt, for example a eutectic mixture of $NaNO_2$ and $KNO_3$. The catalyst is introduced in the form of catalyst bodies into the tubes. In the simplest case, a homogeneous bed is used. A reaction gas containing a mixture of an oxygen-containing gas, usually air, and the hydrocarbon to be oxidized, usually ortho-xylene or naphthalene, is then passed through the bed.

Nowadays, industrial phthalic anhydride catalysts based on $V_2O_5$—$TiO_2$—containing active compositions which are applied as coating to support rings, usually steatite, are used. The oxidation of the hydrocarbon is strongly exothermic, so that, especially in the region of the reactor inlet, evolution of a great deal of heat, which can lead to total oxidation of the hydrocarbon and to deactivation of the catalyst, is observed. To avoid the associated drop in productivity, a change has been made to using structured catalyst beds, i.e. catalyst arrangements, in which zones of catalysts of differing activity are arranged above one another in the tubes. At present, three- or four-zone catalyst beds are usually employed, with a first catalyst zone having a relatively low activity being arranged at the end of the reactor inlet, followed by catalyst zones having an activity which increases stepwise. The catalyst zone having the highest activity is thus arranged at the end of the reactor outlet. Such systems are known from the documents WO 99/61434 A1, WO99/61433 A1 or WO 2004/103944 A1, for example.

Recently, a change has increasingly been made to using catalyst systems having four or more zones, with a relatively short zone made up of a catalyst of relatively high activity firstly being arranged at the reactor inlet end. This zone of relatively high activity is followed by a zone having a lower activity, which is followed by further zones in which the catalyst activity increases again. Such catalyst systems are known, for example, from the documents WO 2007/134849 A1 and WO 2011/032658 A1.

WO 2006/092304 A1 describes the use of a catalyst containing at least one catalyst zone located nearest the gas inlet end, a second catalyst zone located closer to the gas outlet end and a third catalyst zone located even closer to or at the gas outlet end for preparing phthalic anhydride by gas-phase oxidation of o-xylene and/or naphthalene, where the catalyst zones preferably each have an active composition containing $TiO_2$, characterized in that the catalyst activity of the first catalyst zone is higher than the catalyst activity of the second catalyst zone. The activity of the first catalyst zone can be set so that it is higher than the activity of the subsequent second catalyst zone by means of all measures with which a person skilled in the art is familiar. In a preferred embodiment, the increased activity in the first catalyst zone can be achieved, for example, by increasing the bulk density in the first catalyst zone, e.g. by use of another (annular) geometry of the inert shaped body used.

WO 2008/077791 A1 describes a gas-phase oxidation process in which a gaseous stream comprising an aromatic hydrocarbon and molecular oxygen is passed through two or more catalyst zones. Furthermore, this patent document relates to a catalyst system for gas-phase reaction using an initial charge. The product of diameter times height, or the volume of the initially charged inert rings and/or catalyst rings, is smaller than at least one of the subsequent catalyst zones or the ratio of the surface area per unit volume of the initially charged inert rings and/or catalyst rings is greater than at least one of the subsequent catalyst zones.

EP 0985648 A1 relates to the gas-phase oxidation of hydrocarbons, in which a gaseous mixture comprising a gas containing molecular oxygen and hydrocarbons, which may contain substituents, is passed through a fixed catalyst bed, and provides a gas-phase oxidation process which is carried out by passing a gaseous mixture of raw materials through a fixed catalyst bed in which the hollow space content of the catalyst zones increases in one or more steps in the flow direction of the gaseous mixture of raw materials.

The oxidation of ortho-xylene or naphthalene forms not only the desired product of phthalic anhydride but also a series of undesirable by-products formed by incomplete oxidation or by over oxidation. By-products formed by incomplete oxidation are mainly ortho-tolualdehyde and phthalide. By-products formed by over oxidation are mainly carbon monoxide, carbon dioxide and maleic anhydride together with smaller amounts of benzoic acid and citraconic anhydride. A very high selectivity of the oxidation to phthalic anhydride with very small proportions of by-products, including, in particular, maleic anhydride, in the end product combined with a high conversion of the starting material are desirable.

At present, molar selectivities to phthalic anhydride of up to 83 mol % are achieved. In order to increase the selectivity of the oxidation of ortho-xylene or naphthalene to phthalic anhydride further, various parameters of the catalyst system can be varied. Thus, the composition of the catalyst can be varied or the properties of the bed of the catalyst can also be varied. For this purpose, it is possible to vary, for example, the arrangement and the length of the individual catalyst zones.

It is an object of the invention to provide a catalyst arrangement for preparing phthalic anhydride by gas-phase oxidation of aromatic hydrocarbons, which compared to the catalyst arrangements known from the prior art makes an increased yield of phthalic anhydride possible and gives crude phthalic anhydride having a relatively high purity.

The object of the invention is achieved by a catalyst arrangement for preparing phthalic anhydride by gas-phase oxidation of aromatic hydrocarbons, which comprises a reactor having a gas inlet end for a feed gas and a gas outlet end for a product gas and also a first catalyst zone made up of catalyst bodies and at least one second catalyst zone made up of catalyst bodies, where the first catalyst zone is arranged at the gas inlet end and the second catalyst zone is arranged downstream of the first catalyst zone in the gas flow direction and the length of the first catalyst zone in the gas flow direction is less than the length of the second catalyst zone in the gas flow direction, characterized in that the first catalyst zone has a higher gap content compared to the second catalyst zone.

The process of the invention is carried out in one or more reactor(s), with the reactor(s) preferably being tubular (reactor tube or tubes). The openings of the reactor, typically the two openings of the reactor tube, form a reactor inlet for the feed gas and a reactor outlet for the product gas, so that a gas inlet end, a gas outlet end and a gas flow direction are present. The reactor is, for example, heated to a temperature of from 340° C. to 450° C. in a salt bath, with a temperature profile being established as a result of the exothermic reaction and the different catalyst zones possibly present.

The preferably tubular reactor in each case has a diameter (D), which is for the present purposes the internal diameter of the reactor. Preference is given to selecting a diameter (D) of the reactor in the range from 10 to 50 mm, more preferably from 20 to 40 mm. The tubular reactors have a tube length (L) which is likewise selected in conventional ranges, e.g. from 2 to 5 m. The tube length L corresponds to the proportion of the length of the reactor tube which is filled with the catalyst bodies.

The reactor is in each case filled with catalyst bodies which catalyze the gas-phase oxidation of ortho-xylene or naphthalene. The catalyst bodies usually consist of an inert support body which is coated with a vanadium-containing active composition, i.e. the catalytically active composition. According to the invention, at least two catalyst zones have to be formed, where a catalyst zone is a uniform bed of catalyst bodies in the reactor. The extension of the bed in the reactor in the axial direction or in the gas flow direction corresponds to the length $L_x$ of the respective catalyst zone x. If the reactor is configured as a vertical tube, the length of the respective catalyst zone is equivalent to the fill height of the respective catalyst zone. The x-th catalyst zone is counted from the gas inlet end in the gas flow direction. In order to carry out the reaction, from about 2 to 5 standard $m^3$ per hour of air having a loading of from 30 to 100 g of ortho-xylene/standard $m^3$ of air are, for example, passed through the reactor from the top downward at a total pressure of about 1.2-1.6 bar. In general, the successive catalyst zones can follow one another directly, i.e. be in contact, or else can be separated from one another, e.g. by a zone made up of inert bodies.

The first catalyst zone is nearest the gas inlet end of the reactor, followed in the gas flow direction by the at least second catalyst zone consisting of catalyst bodies which differ from the catalyst bodies of the first catalyst zone. According to the invention, the first catalyst zone has a higher gap content than the second catalyst zone.

The first catalyst zone can have a length of less than 1 m, preferably from 10 to 50 cm. The first catalyst zone preferably occupies from 5 to 25%, particularly preferably from 15 to 25%, of the tube length L.

The second catalyst zone can have a length of from 0.3 to 3 m, preferably from 0.85 to 2 m, particularly preferably from 1 to 2 m. The second catalyst zone preferably occupies from 15 to 60%, in particular from 20 to 60% or from 30 to 50%, of the tube length L.

The second catalyst zone can be followed in the gas flow direction by further catalyst zones, e.g. a third catalyst zone which directly adjoins the second catalyst zone, and possibly a fourth catalyst zone which directly adjoins the third catalyst zone. A corresponding fifth catalyst zone is generally not necessary, but is possible.

The third catalyst zone can have a length of less than 1 m, preferably from 50 to 70 cm. The third catalyst zone preferably occupies from about 10 to 30% of the tube length L; especially when the third catalyst zone is the last, i.e. the catalyst zone closest to the reactor outlet, a length of the third catalyst zone of from 20 to 50% of the tube length L is preferred.

The fourth catalyst zone can have a length of from 30 to 150 cm, preferably from 55 to 75 cm. Such a fourth catalyst zone preferably occupies from about 10 to 40%, particularly preferably from 10 to 30%, of the tube length L; especially when the fourth catalyst zone is the last, i.e. the catalyst zone closest to the reactor outlet, a length of the fourth catalyst zone of from 15 to 25% of the tube length L is preferred.

In a further particularly preferred embodiment, the first catalyst zone occupies from 15 to 25% of the tube length L, the second catalyst zone occupies from 20 to 50%, the third catalyst zone occupies from 20 to 50% and the fourth catalyst zone occupies from 15 to 25%.

The gap content GC as a property of a catalyst zone is calculated according to equation 1 (eq. 1).

$$GC=100*(V_{CZ}-V_{FC})/V_{CZ}=100*V_{ES}/V_{CZ} \qquad \text{Eq.1}$$

$V_{CZ}$=total volume of the catalyst zone in the reactor, i.e. $\pi*D^2/4*L_x$ ($L_x$=length of the respective catalyst zone x in the gas flow direction, D=internal diameter of the reactor)
$V_{ES}$=volume of the empty space within the filled catalyst zone
$V_{FC}$=volume of the catalyst bodies within the filled catalyst zone In order to obtain the higher gap content in the first catalyst zone, the catalyst bodies of the first catalyst zone and the second catalyst zone can differ in respect of one or more geometric dimensions and/or in terms of their geometric shape. As geometric shape, preference is given to a cylindrical shape and an annular shape. The geometric dimensions, corresponding to, for example, the height, the length and the width of the catalyst body, are preferably selected so that a volume of the catalyst body in the range from 0.05 to 0.5 $cm^3$ is obtained.

In the simplest case, the catalyst bodies of the second catalyst zone have the same geometric shape as those in the first catalyst zone but are smaller, i.e. have smaller geometric dimensions. The use of rings as catalyst bodies which are smaller in the second catalyst zone than in the first catalyst zone is preferred. However, the reduced gap content can also be realized by means of mixtures of catalyst bodies.

The gap content in the first catalyst zone can be in the range from 62 to 70%, preferably from 64 to 68% and in particular from 65 to 66.5%. The ratio of length to gap content (=100*($L_x/GC_x$) [m]) can be from 0.3 m to 1.2 m, preferably from 0.5 to 0.7 m, in the first catalyst zone. The catalyst bodies of the first catalyst zone preferably have a surface area/volume ratio of from 15 to 17 $cm^{-1}$.

The gap content in the second catalyst zone can be from 60 to 68%, preferably from 62 to 66%, with the proviso that the gap content of the second catalyst zone is lower than that in the first catalyst zone. In particular, the gap content can be in the range from 63 to <65%. The ratio of length to gap content (=100*($L_x/GC_x$) [m]) can be in the range from 1.2 to 4.8 m, preferably from 2.2 to 2.6 m, for the second catalyst zone. The catalyst bodies of the second catalyst zone preferably have a surface area/volume ratio of from >17 to 30 $cm^{-1}$.

The surface area/volume ratio of the catalyst bodies of the first catalyst zone preferably differs from that of the catalyst bodies of the second catalyst zone by more than 5%, more preferably by more than 7%.

If the second catalyst zone is adjoined by a third catalyst zone, preference is given to the third catalyst zone having catalyst bodies which have a gap content which is different from or higher than that of the second catalyst zone. The gap content in the third catalyst zone can be in the range from 62 to 70%, preferably from 64 to 68% and in particular from 65 to 66.5%, with the proviso that the gap content of the third catalyst zone is greater than that of the second catalyst zone. In particular, preference is given to the third catalyst zone having catalyst bodies which form the same gap content as the catalyst bodies of the first catalyst zone. This is preferably achieved by the catalyst bodies of the third catalyst zone having the same geometric shape and the same geometric dimensions as those of the first catalyst zone. The ratio of length to gap content ($=100*L_x/GC_x$[m]) can be in the range from 0.45 to 1.80 m, preferably from 0.7 to 1.1 m, for the third catalyst zone.

If the third catalyst zone is adjoined by a fourth catalyst zone, preference is given to the fourth catalyst zone having catalyst bodies which form the same gap content as the catalyst bodies of the first catalyst zone. This is preferably achieved by the catalyst bodies of the fourth catalyst zone having the same geometric shape and the same geometric dimensions as those of the first catalyst zone. The ratio of length to gap content ($=100*L_x/GC_x$[m]) can be in the range from 0.5 to 1.8 m, preferably from 0.8 to 1.2 m, for the fourth catalyst zone.

The catalyst bodies of the various catalyst zones can also differ in terms of the active composition content. In one embodiment, the catalyst bodies have an active composition content in the range from 3 to 12% by weight, preferably from 4 to 10% by weight, based on the total weight of the catalyst bodies. The active composition content of the first catalyst zone is preferably higher than that of the second catalyst zone. For example, the active composition content of the catalyst bodies of the first catalyst zone can be from 7 to 9% by weight and that of the second catalyst zone can be from 4 to 7% by weight, in each case based on the total weight of the catalyst bodies. As regards any subsequent third and fourth catalyst zone, preference is given to the active composition content $m_A$ increasing from the second to the fourth catalyst zone, or increasing from the second to the third catalyst zone and remaining constant from the third to the fourth catalyst zone.

The active composition can comprise, in addition to vanadium, numerous promoters such as alkali and/or alkaline earth metals, antimony, phosphorus, iron, niobium, cobalt, molybdenum, silver, tungsten, tin, lead, zirconium, copper, gold and/or bismuth and mixtures of two or more of the above components. The catalyst bodies of the individual zones differ, in one embodiment, in terms of the chemical constitution of their active composition. Table 1 gives an overview of the typical chemical constitution of the active composition.

TABLE 1

Typical chemical constitution of the active composition

| Component | Typical content* |
|---|---|
| $V_2O_5$ | From 0.5 to 30% by weight, in particular from 1 to 30% by weight |
| $Sb_2O_3$ or $Sb_2O_5$ | From 0 to 10% by weight |
| Cs | From 0 to 2% by weight |
| P | From 0 to 5% by weight |
| Nb | From 0 to 5% by weight |
| Further components such as Li, Na, K, Ba, W, Mo, Y, Ce, Mg, Sn, Bi, Fe, Ag, Co, Ni, Cu, Au, etc. | From 0 to 5% by weight |
| $TiO_2$ | Balance to 100% by weight |

*The percentages are in each case based on the total weight of the active composition.

The active composition preferably contains from 5 to 15% by weight of $V_2O_5$, from 0 to 5% by weight of $Sb_2O_3$, from 0.2 to 0.75% by weight of Cs, from 0 to 5% by weight of $Nb_2O_5$, in each case based on the total weight of the active composition. Apart from the above components, the balance of the active composition consists entirely or essentially of $TiO_2$. Such an active composition can, for example, be advantageously used in the catalyst bodies of the first or second catalyst zone.

The catalyst bodies preferably have, depending on the catalyst zone, active compositions having different chemical constitutions and/or the active compositions of the individual catalyst zones differ in terms of the physicochemical properties. In one embodiment, the BET surface area of the catalyst or of the active composition is in the range from 15 to about 30 m$^2$/g. However, the active composition can, for example, have a different BET surface area in the catalyst bodies as a function of the respective catalyst zone.

In a preferred embodiment, the BET surface area of the active composition increases from the first catalyst zone to the active composition of the fourth catalyst zone. Suitable ranges for the BET surface area are, for example, from 15 to 25 m$^2$/g for the first catalyst zone, from 15 to 30 m$^2$/g for the second catalyst zone, from 15 to 30 m$^2$/g for the third catalyst zone and from 20 to 45 m$^2$/g for the fourth catalyst zone.

In a particularly preferred embodiment, the active composition of the catalyst bodies of the first catalyst zone contains from 5 to 16% by weight of $V_2O_5$, from 0 to 5% by weight of $Sb_2O_3$, from 0.2 to 0.75% by weight of Cs, from 0 to 1% by weight of P and from 0 to 3% by weight of $Nb_2O_5$, in each case based on the total weight of the active composition. The balance of the active composition consists to an extent of at least 90% by weight, preferably at least 95% by weight, more preferably at least 98% by weight, in particular at least 99% by weight, more preferably at least 99.5% by weight, in particular 100% by weight, of $TiO_2$. In a particularly preferred embodiment, the BET surface area of the $TiO_2$ is in the range from 15 to about 25 m$^2$/g.

In a particularly preferred embodiment, the active composition of the catalyst bodies of the second catalyst zone contains from 5 to 15% by weight of $V_2O_5$, from 0 to 5% by weight of $Sb_2O_3$, from 0.2 to 0.75% by weight of Cs, from 0 to 1% by weight of P and from 0 to 2% by weight of $Nb_2O_5$, in each case based on the total weight of the active composition. The balance of the active composition consists to an extent of at least 90% by weight, preferably at least 95% by weight, more preferably at least 98% by weight, in particular at least 99% by weight, more preferably at least 99.5% by weight, in particular 100% by weight, of $TiO_2$. In a particularly preferred embodiment, the BET surface area of the $TiO_2$ is in the range from 15 to about 45 m$^2$/g.

In a particularly preferred embodiment, the active composition of the catalyst bodies of the third catalyst zone contains from 5 to 15% by weight of $V_2O_5$, from 0 to 4% by weight of $Sb_2O_3$, from 0.05 to 0.5% by weight of Cs, from 0 to 1% by weight of P and from 0 to 2% by weight of $Nb_2O_5$, in each case based on the total weight of the active composition. The balance of the active composition consists to an extent of at least 90% by weight, preferably at least 95% by weight, more preferably at least 98% by weight, in particular at least 99% by weight, more preferably at least 99.5% by weight, in particular 100% by weight, of $TiO_2$. The BET surface area of the $TiO_2$ is preferably in the range from 15 to 25 $m^2/g$.

In a particularly preferred embodiment, the active composition of the catalyst of the fourth catalyst zone contains from 5 to 25% by weight of $V_2O_5$, from 0 to 5% by weight of $Sb_2O_3$, from 0 to 0.2% by weight of Cs, from 0 to 2% by weight of P and from 0 to 1% by weight of $Nb_2O_5$, in each case based on the total weight of the active composition. The balance of the active composition consists to an extent of at least 90% by weight, preferably at least 95% by weight, more preferably at least 98% by weight, in particular at least 99% by weight, more preferably at least 99.5% by weight, in particular 100% by wceight, of $TiO_2$. If the fourth catalyst zone is the (last) catalyst zone closest to the gas outlet end of the reactor, preference is given to a BET surface area of the $TiO_2$ which is somewhat higher than that of the $TiO_2$ of the catalyst zones closer to the gas inlet end. The $TiO_2$ of the active composition of the fourth catalyst zone is preferably in the range from about 15 to about 45 $m^2/g$.

Furthermore, the catalyst bodies of the individual catalyst zones can differ in terms of their intrinsic activity; the different intrinsic activity can, for example, be obtained by means of a different chemical constitution of the active composition. According to the invention, preference is given to the catalyst bodies of the first catalyst zone having a higher intrinsic activity than the catalyst bodies of the second catalyst zone.

For the purposes of the present invention, the intrinsic activity of a catalyst body $C_b$ is the activity of the active composition for a particular reaction under conditions under which the reaction proceeds over an infinitesimally small catalyst particle and the reaction is not influenced by the neighboring particles. Such conditions would correspond to a temperature gradient over the reactor of 0° C., an infinite space-time velocity of the gas and an infinite distance between the infinitesimally small catalyst particles. Such an intrinsic activity can be determined, for example, by means of a series of experiments which makes it possible to extrapolate the activity of the catalyst body in a state corresponding to such an ideal state (e.g. extrapolation of the experimental results to a conversion of zero).

In the practical determination of the intrinsic activity, in one embodiment, a catalyst body having a particular geometry and a particular content of active composition is produced. Furthermore, it is assumed that the reaction is a first order reaction, regardless of the order according to which the reaction actually proceeds. This standardized catalyst body is then diluted with inert bodies so that the temperature difference between the gas inlet end and the gas outlet end is less than 25° C., preferably less than 10° C., i.e. the reaction proceeds under virtually isothermal conditions, with the pressure drop over the reactor being less than 30 mbar, preferably less than 10 mbar, and the conversion being set to a value in the range from 65 to 95%.

For this purpose, the catalyst body is diluted with inert bodies. The geometry of the catalyst bodies and the inert bodies is selected so that the required low pressure drop is achieved. The ratio of inert bodies to catalyst bodies is selected so that the required conversion is achieved and at the same time the heat evolution is so low that the required small temperature difference between gas inlet and gas outlet is maintained. Based on the volume, which is determined by the bulk density of the catalyst bodies and the inert bodies, a ratio of catalyst bodies to inert bodies of from 1:5 to 1:10 is preferably selected. The dimensions of the test reactor are, depending on the reaction in question, selected in the range from 1 to 6 m for the length and from 18 to 32 mm for the diameter of the reactor. In the case of fast reactions, a short length is selected, while for reactions which proceeds slowly, a greater reaction distance is required in order to achieve the desired conversions.

The conversion of the reaction catalyzed by the active composition of the catalyst body is then measured at particular space-time velocities and at various particular temperatures. From the conversions, the active composition-based activity constant A* of the catalyst can then be calculated as a function of the conversion according to eq. 2:

$$A^* = \frac{[GHSV \times -1 \times \ln(1 - Conv)]}{[m_{activecomposition}]} \quad \text{Eq. 2}$$

Here:
A*: active composition-based activity constant of the active composition at a particular temperature and GHSV;
GHSV: space-time velocity $[h^{-1}]$
$m_{activecomposition}$: amount of active composition introduced into the reactor [g];
Conv: conversion of the starting material, with Conv being calculated according to eq. 3.

$$Conv = \frac{M_{in} - M_{out}}{M_{in}} \quad \text{Eq. 3}$$

$M_{in}$: amount of starting material [mol] fed to the catalyst charge
$M_{out}$: amount of starting material [mol] leaving the catalyst charge From the determined active composition-based activity constants A* as a function of the conversion Conv, the intrinsic activity $A_{ib}$ of the catalyst is then determined by linear extrapolation to a conversion of zero. The conversions to be set for the extrapolation are selected so that they are in the linear region of the dependence of the active composition-based activity constant as a function of conversion (e.g. conversion in the range from 60% to 90%).

A temperature profile is established during operation of the catalyst arrangement of the invention. The temperature profile is preferably such that the maximum temperature in the first catalyst zone is from 10 to 100° C. lower, more preferably from 20 to 90° C. lower, most preferably from 30 to 70° C. lower, than that in the second catalyst zone during the gas-phase oxidation of aromatic hydrocarbons.

If a third catalyst zone is present, the intrinsic activity of the third catalyst zone is preferably higher than that of the second catalyst zone. A temperature profile which decreases from the second catalyst zone to the third catalyst zone is preferably established during the reaction. In particular, the temperature profile is such that the maximum temperature in the third catalyst zone is from 10 to 100° C. lower, more preferably from 20 to 90° C. lower, most preferably from 30 to 70° C. lower, than in the second catalyst zone during the gas-phase oxidation of hydrocarbons.

If a fourth catalyst zone is present, the intrinsic activity of the fourth catalyst zone is preferably higher than that of the third catalyst zone. Here, the temperature profile preferably decreases from the second to the fourth (and also to the third) catalyst zone ($T_2 > T_3 > T_4$, in each case based on the maximum temperature in each zone). In particular, the temperature profile is such that the maximum temperature in the fourth catalyst zone is from 10 to 100° C. lower, more preferably from 20 to 90° C. lower, most preferably from 30 to 70° C. lower, than in the second catalyst zone and from 1 to 50° C. lower, more preferably from 5 to 25° C. lower, most preferably from 5 to 10° C. lower, than in the third catalyst zone during the gas-phase oxidation of hydrocarbons.

In particular, preference is given to the intrinsic activity decreasing from the first to the second catalyst zone and then rising from the second to the fourth catalyst zone ($A_1 > A_2 < A_3 < A_4$, where A=intrinsic activity of the active composition in the respective zone). Furthermore, preference is given to the temperature profile rising from the first to the second catalyst zone, decreasing from the second to the fourth catalyst zone ($T_1 < T_2 > T_3 > T_4$, in each case based on the maximum temperature in each zone) and a temperature maximum being formed in the second catalyst zone.

The catalyst bodies consist of an inert support body and an active composition applied thereto. The catalyst bodies of the catalyst zones are prepared in the usual way, with a thin layer of the active composition being applied to the inert support body. For example, a suspension of the active composition or a solution or suspension of precursor compounds which can be converted into the components of the active composition can be sprayed onto the inert support. This can, for example, be carried out at a temperature of from 80 to 200° C. in a fluidized bed. However, the active composition can also, for example, be applied to the inert support in a type of coating drum.

For the coating operation, the aqueous solution or suspension of active components and an organic binder, preferably a copolymer of vinyl acetate-vinyl laurate, vinyl acetate-ethylene or styrene-acrylate, is sprayed via one or more nozzles onto the heated, fluidized support. It is particularly advantageous to introduce the spray liquid at the position of greatest product velocity, as a result of which the sprayed material can become uniformly distributed in the bed. The spraying operation is continued until either the suspension has been consumed or the required amount of active components has been applied to the support. For the purposes of the present invention, active components are components of the active composition, especially metal compounds present in the active composition. The active components can be used as oxides or in the form of precursor compounds. For the purposes of the present invention, precursor compounds are compounds which, for example, can be converted into the components of the active composition, i.e. the oxides, by heating in air. Suitable precursor compounds are, for example, nitrates, sulfates, carbonates, acetates or chlorides of the metals.

In one embodiment, the active composition is applied in a moving bed or fluidized bed with the aid of suitable binders so as to produce a coated catalyst. Suitable binders encompass organic binders with which a person skilled in the art will be familiar, preferably copolymers, advantageously in the form of an aqueous suspension of vinyl acetate-vinyl laurate, vinyl acetate-acrylate, styrene, acrylate, vinyl acetate-maleate or vinyl acetate-ethylene. Particular preference is given to using an organic polymeric or copolymeric adhesive, in particular a vinyl acetate copolymer adhesive, as binder. The binder used is added in customary amounts to the active composition, for example in an amount of from about 10 to 20% by weight based on the solids content of the active composition. For example, reference may be made to EP 744214.

The determination of the binder content is carried out by calcining the coated catalyst bodies at 450° C. for 7 hours, resulting in the organic binder being completely thermally decomposed. The binder content is determined after the calcination according to a eq. 4:

$$A_B = \frac{M_I - M_O}{M_I} * 100\% \qquad \text{Eq. 4}$$

$A_B$=binder content
$M_I$=weight of catalyst before calcination
$M_O$=weight of catalyst after calcination The physicochemical characterization of the active composition (BET, chemical analysis) is carried out by, after thermal decomposition of the binder, separating the active composition mechanically by means of a sieve from the support rings. The remaining part of the active composition still adhering to the support rings is removed completely by ultrasonic treatment. The washed support rings are subsequently dried at 120° C. in a drying oven and weighed. The proportion of active composition is subsequently determined according to eq. 5:

$$A_A = \frac{M_O - M_S}{M_O} * 100\% \qquad \text{Eq. 5}$$

$A_A$=proportion of active composition
$M_O$=weight of catalyst after calcination
$M_S$=weight of support rings The determination of the specific surface area of the materials is carried out by the BET method in accordance with DIN 66131; a publication of the BET method may also be found in J. Am. Chem. Soc. 60, 309 (1938). The sample to be measured was dried at 350° C. under reduced pressure in a silica tube (F=50 ml(min) for 1.5 hours). The reactor was then cooled to room temperature, evacuated and dipped into a Dewar vessel containing liquid nitrogen. The nitrogen adsorption was carried out at 77 K using an RXM 100 sorption system (Advanced Scientific Design, Inc.).

EXAMPLES

Catalytic measurements were carried out on four-zone catalyst arrangements made up of catalyst bodies. To synthesize the catalyst bodies, three different types of steatite rings designated as ring 8×6×5, ring 7×7×4 and ring 6×5×4 were used as shaped bodies. The nomenclature of the geometric dimensions of the rings corresponds to external diameter (Da) [mm]×height (H) [mm]×internal diameter (Di) [mm]. The geometric dimensions of the uncoated shaped bodies can be seen in table 2. The uncoated shaped bodies were introduced into a coating apparatus and coated homogeneously with the active composition.

During the coating operation, an aqueous suspension of the active components and an organic binder is sprayed through a plurality of nozzles onto the heated, fluidized support until an active composition layer of about 50-150 µm has been formed. Table 3 gives an overview of the catalyst bodies used and the respective chemical constitution of the active composition.

The gap content GC of the catalyst zones was calculated using eq. 6.

$$GC = \left[1 - \frac{\rho_{bulk}}{\rho_{cat}}\right] * 100\% \qquad \text{Eq. 6}$$

$\rho_{bulk}$=bulk density of the catalyst bodies [g/cm$^3$]
$\rho_{cat}$=apparent density of the catalyst bodies [g/cm$^3$] (about 2.5 g/cm$^3$)
GC=gap content [%]

To determine the bulk density, a tube having a diameter close to the internal diameter of the reactor tube (internal diameter 2.7 cm) was filled with the appropriate catalyst, in each case to a fill height of 100.0 cm. To ensure uniform filling, the catalyst bodies were introduced individually into the tube. Uniform filling could be visually monitored since a transparent plastic tube was used. After successful filling, the tube was completely emptied and the mass of the catalyst bodies which had been introduced was determined by means of a balance. The bulk density of the catalyst bodies was calculated therefrom according to eq. 7 below:

$$\rho_{bulk} = \frac{m_{cat}}{\pi \frac{d^2}{4} h} \qquad \text{Eq. 7}$$

$\rho_{bulk}$: bulk density of catalyst bodies [g/cm$^3$]
$m_{cat}$: mass of catalyst bodies introduced [g]
d: internal diameter of tube [cm]=2.7 cm
h: fill height of tube [cm]=100.0 cm The bulk density was determined three times for each type of catalyst body in order to calculate therefrom the arithmetic mean used in the further text.

The apparent density of the catalyst bodies corresponds to the ratio of the total mass of the catalyst body (i.e. including the mass of the steatite ring and the applied active composition) to the total volume of the shaped body taking into account the outer surface. The total volume of the shaped body corresponds to the volume of the shaped body including the volume of any pores present. The apparent density was determined by means of a mercury porosimeter; owing to the fact that mercury does not wet the walls of a solid sample, pressure is required to intrude into any pores in the sample. This enables the total volume to be determined, since the system of sample+mercury is under reduced pressure and mercury therefore cannot penetrate into the interior of the pores and so then covers exclusively the external surface.

The apparent density of the various catalyst bodies in table 3 varies by values of <0.05 g/cm$^3$.

To form the catalyst zones, the respective catalyst bodies were introduced into a salt bath-cooled tube having an internal diameter of 25 mm and a length of 4 m. A 3 mm thermocoupled sheath having an installed withdrawable element for measuring the temperature was arranged centrally in the tube.

To carry out the catalytic measurement, from about 3.7 to 4.0 standard m$^3$ (standard cubic meters) per hour of air having a loading of from 30 to 100 g of ortho-xylene/standard m$^3$ of air (purity of ortho-xylene >98%) were passed at a total pressure of about 1500 mbar from the top downward through the tube. The measurements were in each case carried out at a loading of from about 40 to 100 g of ortho-xylene/standard m$^3$ of air and a salt bath temperature in the range from 350 to 390° C.

The phthalic anhydride yield was calculated using eq. 8:

$$Y_{PA} = \left[139.52 - \left(800 * \frac{A+B}{E}\right) + (100 - F) - (1.25 * H) - (1.1 * G)\right] \qquad \text{Eq. 8}$$

A=CO$_2$ in the product stream [% by volume]
B=CO in the product stream [% by volume]
H=maleic anhydride in the product stream [% by weight]
E=ortho-xylene loading in the feed stream [g/standard m$^3$/h/tube]
F=ortho-xylene purity of the ortho-xylene used [% by weight]
G=ortho-xylene breakthrough based on the total ortho-xylene used [% by weight]
$Y_{PA}$=yield of phthalic anhydride (PAn) based on the total weight of the ortho-xylene used [% by weight]

As can be seen from eq. 8, the phthalic anhydride yield is directly dependent on the formation of the three most important by-products CO, CO$_2$ and maleic anhydride.

TABLE 2

Geometric dimensions and properties of the uncoated shaped bodies

|  | Ring 8 × 6 × 5 | Ring 7 × 7 × 4 | Ring 6 × 5 × 4 |
|---|---|---|---|
| External diameter × height [cm$^2$] | 0.48 | 0.28 | 0.30 |
| Volume [cm$^3$] | 0.184 | 0.104 | 0.079 |
| Surface area [cm$^2$] | 3.063 | 1.901 | 1.885 |
| Surface area/volume [cm$^{-1}$] | 16.7 | 18.3 | 24.0 |
| Volume/surface area [cm] | 0.060 | 0.055 | 0.042 |
| Apparent density [g/cm$^3$] | 2.61 | 2.61 | 2.61 |

TABLE 3

Catalyst bodies used

| Designation | Ring shape (Da × H × Di)[1] [mm] | Proportion of binder [% by weight][3] | Proportion of active composition [% by weight][2] | BET [m$^2$/g] | TiO$_2$ [% by weight][3] | V$_2$O$_5$ [% by weight][3] | Promoters [% by weight][4] |
|---|---|---|---|---|---|---|---|
| Comparative test 1 | | | | | | | |
| A0 | 8 × 6 × 5 | 2.3 | 8.5 | 18 | 87.4 | 7.5 | 5.1 |
| A1 | 8 × 6 × 5 | 2.3 | 8.5 | 18 | 87.4 | 7.5 | 5.1 |
| A2 | 8 × 6 × 5 | 2.3 | 8.0 | 18 | 89.0 | 7.5 | 3.5 |
| A3 | 8 × 6 × 5 | 2.3 | 8.0 | 27 | 90.6 | 9.0 | 0.4 |

TABLE 3-continued

Catalyst bodies used

| Designation | Ring shape (Da × H × Di)[1] [mm] | Proportion of binder [% by weight][3] | Proportion of active composition [% by weight][2] | BET [m²/g] | TiO₂ [% by weight][3] | V₂O₅ [% by weight][3] | Promoters [% by weight][4] |
|---|---|---|---|---|---|---|---|
| Comparative test 2 | | | | | | | |
| B0 | 8 × 6 × 5 | 2.4 | 8.3 | 19 | 87.4 | 7.5 | 5.1 |
| B1 | 8 × 6 × 5 | 2.4 | 8.6 | 18 | 87.3 | 7.6 | 5.1 |
| B2.1 | 8 × 6 × 5 | 2.4 | 8.0 | 18 | 89.1 | 7.4 | 3.5 |
| B3.1 | 8 × 6 × 5 | 2.2 | 7.9 | 26 | 90.6 | 9.1 | 0.4 |
| Test 1 according to the invention | | | | | | | |
| B1 | 8 × 6 × 5 | 2.4 | 8.6 | 18 | 87.3 | 7.6 | 5.1 |
| D1 | 6 × 5 × 4 | 2.3 | 5.3 | 19 | 84.7 | 7.2 | 8.1 |
| B2.1 | 8 × 6 × 5 | 2.4 | 8.0 | 18 | 89.1 | 7.4 | 3.5 |
| B3.2 | 8 × 6 × 5 | 2.4 | 7.9 | 25 | 90.2 | 9.4 | 0.4 |
| Test 2 according to the invention | | | | | | | |
| B0 | 8 × 6 × 5 | 2.4 | 8.3 | 19 | 87.4 | 7.5 | 5.1 |
| E1 | 6 × 5 × 4 | 2.2 | 5.3 | 24 | 83.7 | 10.7 | 5.6 |
| B2.1 | 8 × 6 × 5 | 2.4 | 8.0 | 18 | 89.1 | 7.4 | 3.5 |
| B3.2 | 8 × 6 × 5 | 2.4 | 7.9 | 25 | 90.2 | 9.4 | 0.4 |
| Test 3 according to the invention | | | | | | | |
| B0 | 8 × 6 × 5 | 2.4 | 8.3 | 19 | 87.4 | 7.5 | 5.1 |
| F1 | 7 × 7 × 4 | 2.2 | 5.3 | 27 | 83.0 | 10.6 | 5.6 |
| B2.2 | 8 × 6 × 5 | 2.4 | 8.0 | 18 | 88.0 | 7.4 | 3.5 |
| B3.1 | 8 × 6 × 5 | 2.2 | 7.9 | 26 | 90.6 | 9.1 | 0.4 |

[1] Da = external diameter, H = height, Di = internal diameter
[2] based on the total weight of the catalyst body
[3] based on the total weight of the active composition
[4] predominantly Sb₂O₃ with smaller proportions of Nb₂O₅, P and Cs

TABLE 4

Fill parameters for the comparative test 1

| Catalyst zone x | Catalyst | Fill height $L_x$ [cm] | Bulk density [g/cm³] | Apparent density [g/cm³] | Gap content, GC [%] | Ring shape (Da × H × Di) [mm] |
|---|---|---|---|---|---|---|
| 1 | A0 | 40.9 | 0.92 | 2.623 | 65.1 | 8 × 6 × 5 |
| 2 | A1 | 160.0 | 0.91 | 2.664 | 65.8 | 8 × 6 × 5 |
| 3 | A2 | 60.9 | 0.91 | 2.622 | 65.3 | 8 × 6 × 5 |
| 4 | A3 | 59.5 | 0.91 | 2.663 | 65.8 | 8 × 6 × 5 |

TABLE 5

Fill parameters for the comparative test 2

| Catalyst zone x | Catalyst | Fill height $L_x$ [cm] | Bulk density [g/cm³] | Apparent density [g/cm³] | Gap content, GC [%] | Ring shape (Da × H × Di) [mm] |
|---|---|---|---|---|---|---|
| 1 | B0 | 40.0 | 0.89 | 2.624 | 66.0 | 8 × 6 × 5 |
| 2 | B1 | 135.3 | 0.91 | 2.610 | 65.2 | 8 × 6 × 5 |
| 3 | B2.1 | 60.5 | 0.90 | 2.619 | 65.8 | 8 × 6 × 5 |
| 4 | B3.1 | 64.9 | 0.92 | 2.643 | 65.2 | 8 × 6 × 5 |

TABLE 6

Fill parameters for test 1 according to the invention

| Catalyst zone x | Catalyst | Fill height $L_x$ [cm] | Bulk density [g/cm³] | Apparent density [g/cm³] | Gap content, GC [%] | Ring shape (Da × H × Di) [mm] |
|---|---|---|---|---|---|---|
| 1 | B1 | 39.8 | 0.84 | 2.610 | 65.2 | 8 × 6 × 5 |
| 2 | D1 | 154.5 | 0.91 | 2.631 | 62.6 | 6 × 5 × 4 |
| 3 | B2.1 | 60.5 | 0.84 | 2.619 | 65.8 | 8 × 6 × 5 |
| 4 | B3.2 | 64.8 | 0.84 | 2.620 | 65.0 | 8 × 6 × 5 |

TABLE 7

Fill parameters for test 2 according to the invention

| Catalyst zone x | Catalyst | Fill height $L_x$ [cm] | Bulk density [g/cm³] | Apparent density [g/cm³] | Gap content, GC [%] | Ring shape (Da × H × Di) [mm] |
|---|---|---|---|---|---|---|
| 1 | B0 | 39.7 | 0.89 | 2.624 | 66.0 | 8 × 6 × 5 |
| 2 | E1 | 155.3 | 0.96 | 2.693 | 64.5 | 6 × 5 × 4 |
| 3 | B2.1 | 60.9 | 0.90 | 2.619 | 65.8 | 8 × 6 × 5 |
| 4 | B3.2 | 64.3 | 0.92 | 2.620 | 65.0 | 8 × 6 × 5 |

TABLE 8

Fill parameters for test 3 according to the invention

| Catalyst zone x | Catalyst | Fill height $L_x$ [cm] | Bulk density [g/cm³] | Apparent density [g/cm³] | Gap content, GC [%] | Ring shape (Da × H × Di) [mm] |
|---|---|---|---|---|---|---|
| 1 | B0 | 41.0 | 0.89 | 2.62 | 66.0 | 8 × 6 × 5 |
| 2 | F1 | 155.0 | 0.93 | 2.60 | 64.1 | 7 × 7 × 4 |
| 3 | B2.2 | 60.5 | 0.88 | 2.57 | 65.7 | 8 × 6 × 5 |
| 4 | B3.1 | 64.5 | 0.92 | 2.64 | 65.2 | 8 × 6 × 5 |

TABLE 9

Catalyst performance in the comparative test 1

| TOS [h] | Volume flow of air [Nm³] | Loading with ortho-xylene [g/Nm³/h/tube] | SBT [°C.] | CO [% by volume][1] | $CO_2$ [% by volume][1] | MAn [% by weight][2] | ortho-Xylene [% by weight][2] | Yield of PAn [% by weight][3] | (CO + $CO_2$)/ Loading [Vol.-%/g/Nm³/h/tube] |
|---|---|---|---|---|---|---|---|---|---|
| 178.6 | 4.0 | 33.7 | 379 | 0.337 | 0.781 | 5.0 | 0.01 | 108.7 | 0.0332 |
| 203.4 | 4.0 | 35.7 | 378 | 0.357 | 0.827 | 5.1 | 0.01 | 108.7 | 0.0332 |
| 705.1 | 4.0 | 46.3 | 371 | 0.465 | 1.115 | 4.9 | 0.02 | 108.0 | 0.0341 |
| 728.7 | 4.0 | 48.3 | 370 | 0.487 | 1.193 | 5.0 | 0.02 | 107.5 | 0.0348 |
| 752.2 | 4.0 | 48.3 | 370 | 0.490 | 1.137 | 5.0 | 0.02 | 108.3 | 0.0337 |
| 2821.4 | 4.0 | 79.9 | 359 | 0.749 | 1.785 | 4.5 | 0.03 | 110.5 | 0.0317 |
| 2847.0 | 4.0 | 79.9 | 360 | 0.752 | 1.798 | 4.5 | 0.03 | 110.3 | 0.0319 |
| 2867.2 | 4.0 | 81.4 | 360 | 0.757 | 1.810 | 4.5 | 0.03 | 110.7 | 0.0315 |

TABLE 10

Catalyst performance in the comparative test 2

| TOS [h] | Volume flow of air [Nm³] | Loading with ortho-xylene [g/Nm³/h/tube] | SBT [°C.] | CO [% by volume][1] | $CO_2$ [% by volume][1] | MAn [% by weight][2] | ortho-Xylene [% by weight][2] | Yield of PAn [% by weight][3] | (CO + $CO_2$)/ Loading [Vol.-%/g/Nm³/h/tube] |
|---|---|---|---|---|---|---|---|---|---|
| 254.3 | 3.7 | 73.1 | 368 | 0.758 | 1.712 | 4.9 | 0.02 | 108.4 | 0.0338 |
| 278.4 | 3.7 | 73.1 | 368 | 0.732 | 1.671 | 4.7 | 0.02 | 109.3 | 0.0328 |
| 302.5 | 3.7 | 73.1 | 368 | 0.726 | 1.670 | 4.7 | 0.02 | 109.5 | 0.0328 |
| 538.1 | 3.7 | 82.0 | 364 | 0.806 | 1.866 | 4.7 | 0.02 | 109.6 | 0.0326 |
| 562.1 | 3.7 | 83.9 | 363 | 0.820 | 1.958 | 4.7 | 0.03 | 109.2 | 0.0331 |
| 761.3 | 3.7 | 90.9 | 356 | 0.848 | 2.048 | 4.3 | 0.02 | 110.6 | 0.0319 |
| 785.3 | 3.7 | 90.9 | 356 | 0.848 | 2.056 | 4.3 | 0.03 | 110.6 | 0.0320 |
| 809.3 | 3.7 | 90.9 | 356 | 0.838 | 2.038 | 4.2 | 0.03 | 110.9 | 0.0316 |

[1] based on the total volume of the product stream
[2] based on the total weight of the product stream
[3] based on the total weight of the xylene used

TABLE 11

Catalyst performance in test 1 according to the invention

| TOS [h] | Volume flow of air [Nm³] | Loading with ortho-xylene [g/Nm³/h/tube] | SBT [°C.] | CO [% by volume][1] | $CO_2$ [% by volume][1] | MAn [% by weight][2] | ortho-Xylene [% by weight][2] | Yield of PAn [% by weight][3] | (CO + $CO_2$)/ Loading [Vol.-%/g/Nm³/h/tube] |
|---|---|---|---|---|---|---|---|---|---|
| 318.6 | 4.0 | 38.9 | 382 | 0.390 | 0.830 | 4.1 | 0.01 | 111.3 | 0.0313 |
| 342.5 | 4.0 | 39.9 | 380 | 0.398 | 0.854 | 4.0 | 0.01 | 111.5 | 0.0313 |
| 532.7 | 4.0 | 45.9 | 372 | 0.436 | 0.958 | 3.7 | 0.01 | 112.6 | 0.0304 |
| 557.9 | 4.0 | 48.1 | 370 | 0.447 | 0.989 | 3.7 | 0.01 | 113.1 | 0.0299 |
| 579.6 | 4.0 | 50.1 | 369 | 0.458 | 1.033 | 3.6 | 0.02 | 113.2 | 0.0298 |
| 680.8 | 4.0 | 54.0 | 365 | 0.479 | 1.089 | 3.6 | 0.02 | 113.8 | 0.0290 |
| 698.9 | 4.0 | 56.0 | 364 | 0.494 | 1.136 | 3.6 | 0.02 | 113.8 | 0.0291 |
| 916.5 | 4.0 | 63.9 | 362 | 0.530 | 1.321 | 3.6 | 0.03 | 113.8 | 0.0289 |

[1] based on the total volume of the product stream
[2] based on the total weight of the product stream
[3] based on the total weight of the xylene used

TABLE 12

Catalyst performance in test 2 according to the invention

| TOS [h] | Volume flow of air [Nm³] | Loading with ortho-xylene [g/Nm³/h/tube] | SBT [° C.] | CO [% by volume][1] | $CO_2$ [% by volume][1] | MAn [% by weight][2] | ortho-Xylene [% by weight][2] | Yield of PAn [% by weight][3] | (CO + $CO_2$)/Loading [Vol.-%/g/Nm³/h/tube] |
|---|---|---|---|---|---|---|---|---|---|
| 156.2 | 4.0 | 43.0 | 387 | 0.463 | 1.019 | 4.6 | 0.01 | 108.2 | 0.0345 |
| 180.4 | 4.0 | 47.0 | 384 | 0.508 | 1.115 | 4.7 | 0.01 | 108.0 | 0.0345 |
| 204.3 | 4.0 | 51.0 | 381 | 0.560 | 1.230 | 4.8 | 0.01 | 107.5 | 0.0351 |
| 229.5 | 4.0 | 55.9 | 377 | 0.595 | 1.317 | 4.7 | 0.01 | 108.3 | 0.0342 |
| 250.5 | 4.0 | 59.9 | 373 | 0.581 | 1.318 | 4.3 | 0.02 | 110.7 | 0.0317 |
| 274.5 | 4.0 | 59.9 | 373 | 0.587 | 1.332 | 4.3 | 0.02 | 110.5 | 0.0320 |
| 298.5 | 4.0 | 59.9 | 373 | 0.585 | 1.335 | 4.3 | 0.02 | 110.5 | 0.0321 |
| 348.5 | 4.0 | 66.1 | 367 | 0.578 | 1.408 | 3.9 | 0.03 | 112.6 | 0.0300 |
| 1260.8 | 4.0 | 78.0 | 357 | 0.636 | 1.585 | 3.3 | 0.08 | 114.5 | 0.0285 |
| 1284.9 | 4.0 | 78.0 | 357 | 0.633 | 1.539 | 3.2 | 0.07 | 115.2 | 0.0279 |
| 1309.0 | 4.0 | 78.0 | 357 | 0.623 | 1.511 | 3.2 | 0.07 | 115.6 | 0.0274 |
| 1335.1 | 4.0 | 80.9 | 357 | 0.636 | 1.587 | 3.2 | 0.09 | 115.5 | 0.0275 |
| 1383.6 | 4.0 | 84.9 | 356 | 0.676 | 1.650 | 3.5 | 0.10 | 115.2 | 0.0274 |
| 1406.4 | 4.0 | 84.9 | 355 | 0.681 | 1.663 | 3.5 | 0.09 | 115.0 | 0.0276 |
| 1551.6 | 4.0 | 84.9 | 355 | 0.677 | 1.731 | 3.5 | 0.13 | 114.4 | 0.0284 |
| 1578.4 | 4.0 | 84.9 | 355 | 0.648 | 1.747 | 3.5 | 0.12 | 114.5 | 0.0282 |
| 1621.3 | 4.0 | 84.9 | 355 | 0.674 | 1.717 | 3.5 | 0.13 | 114.5 | 0.0282 |

TABLE 13

Catalyst performance in test 3 according to the invention

| TOS [h] | Volume flow of air [Nm³] | Loading with ortho-xylene [g/Nm³/h/tube] | SBT [° C.] | CO [% by volume][1] | $CO_2$ [% by volume][1] | MAn [% by weight][2] | ortho-Xylene [% by weight][2] | Yield of PAn [% by weight][3] | (CO + $CO_2$)/Loading [Vol.-%/g/Nm³/h/tube] |
|---|---|---|---|---|---|---|---|---|---|
| 164.3 | 4.0 | 40.6 | 386 | 0.465 | 0.900 | 4.5 | 0.01 | 109.0 | 0.0336 |
| 184.2 | 4.0 | 43.2 | 382 | 0.480 | 0.944 | 4.5 | 0.01 | 109.5 | 0.0330 |
| 207.6 | 4.0 | 46.2 | 378 | 0.511 | 1.072 | 4.3 | 0.02 | 108.7 | 0.0343 |
| 231.6 | 4.0 | 46.2 | 378 | 0.506 | 1.060 | 4.3 | 0.02 | 109.0 | 0.0339 |
| 255.6 | 4.0 | 46.2 | 378 | 0.506 | 1.070 | 4.3 | 0.00 | 108.8 | 0.0341 |
| 279.6 | 4.0 | 51.2 | 374 | 0.559 | 1.197 | 4.3 | 0.02 | 108.8 | 0.0343 |
| 309.8 | 4.0 | 55.3 | 370 | 0.567 | 1.229 | 4.2 | 0.03 | 110.3 | 0.0325 |
| 333.8 | 4.0 | 61.3 | 367 | 0.637 | 1.417 | 4.1 | 0.03 | 109.6 | 0.0335 |
| 351.5 | 4.0 | 65.4 | 365 | 0.657 | 1.470 | 4.2 | 0.04 | 110.2 | 0.0325 |
| 387.6 | 4.0 | 71.4 | 363 | 0.705 | 1.608 | 4.1 | 0.03 | 110.4 | 0.0324 |
| 404.3 | 4.0 | 71.4 | 363 | 0.684 | 1.559 | 3.9 | 0.03 | 111.5 | 0.0314 |
| 428.3 | 4.0 | 71.4 | 363 | 0.671 | 1.534 | 3.9 | 0.03 | 111.9 | 0.0309 |
| 452.3 | 4.0 | 79.5 | 362 | 0.793 | 1.839 | 4.2 | 0.04 | 109.8 | 0.0331 |
| 474.4 | 4.0 | 82.5 | 362 | 0.814 | 1.902 | 4.2 | 0.04 | 109.9 | 0.0329 |
| 498.4 | 4.0 | 87.9 | 361 | 0.870 | 2.053 | 4.2 | 0.05 | 109.6 | 0.0333 |
| 522.4 | 3.9 | 87.9 | 360 | 0.855 | 2.032 | 4.1 | 0.05 | 110.0 | 0.0329 |
| 546.3 | 3.9 | 89.9 | 359 | 0.849 | 2.028 | 4.0 | 0.07 | 110.8 | 0.0320 |
| 570.4 | 3.9 | 89.9 | 359 | 0.846 | 2.039 | 4.0 | 0.07 | 110.8 | 0.0321 |
| 618.4 | 3.9 | 93.9 | 358 | 0.891 | 2.171 | 4.0 | 0.11 | 110.3 | 0.0326 |

[1]based on the total volume of the product stream
[2]based on the total weight of the product stream
[3]based on the total weight of the xylene used

The invention claimed is:

1. A catalyst arrangement for preparing phthalic anhydride by gas-phase oxidation of aromatic hydrocarbons, comprising a reactor having a gas inlet end for a feed gas and a gas outlet end for a product gas and also a first catalyst zone made up of catalyst bodies and at least one second catalyst zone made up of catalyst bodies, where the first catalyst zone is arranged at the gas inlet end and the second catalyst zone is arranged downstream of the first catalyst zone in the gas flow direction and the length of the first catalyst zone in the gas flow direction is less than the length of the second catalyst zone in the gas flow direction, wherein the first catalyst zone has a higher gap content compared to the second catalyst zone and wherein the gap content of the first catalyst zone is at least 0.6% higher than the gap content of the second catalyst zone.

2. The catalyst arrangement as claimed in claim 1, wherein the higher gap content is due to the catalyst bodies of the first catalyst zone differing in terms of one or more geometric dimension(s), their geometric shape from the catalyst bodies of the second catalyst zone or both.

3. The catalyst arrangement as claimed in claim 2, wherein the catalyst bodies of the first catalyst zone and the catalyst bodies of the second catalyst zone are ring-shaped and the catalyst bodies of the second catalyst zone have smaller geometric dimensions than those of the first catalyst zone.

4. The catalyst arrangement as claimed in claim 1, wherein the gap content of the first catalyst zone is at least 1.5% higher than the gap content of the second catalyst zone.

5. The catalyst arrangement as claimed in claim 1, wherein the catalyst bodies of the first catalyst zone have, in each case based on the mass of the catalyst bodies, a higher active composition loading than the catalyst bodies of the second catalyst zone.

6. The catalyst arrangement as claimed in claim 1, wherein the active composition of the catalyst bodies of the first catalyst zone has a lower BET surface area than the active composition of the catalyst bodies of the second catalyst zone.

7. The catalyst arrangement as claimed in claim 1, wherein the catalyst bodies of the first catalyst zone have an active composition having a lower percentage $V_2O_5$ content, based on the mass of the active composition, than the catalyst bodies of the second catalyst zone.

8. The catalyst arrangement as claimed in claim 1, wherein the catalyst bodies of the first catalyst zone have an active composition having a lower percentage promoter content, based on the mass on the active composition, than the catalyst bodies of the second catalyst zone.

9. The catalyst arrangement as claimed in claim 1, wherein a third catalyst zone which has a higher gap content compared to the second catalyst zone is arranged downstream of the second catalyst zone in the gas flow direction.

10. The catalyst arrangement as claimed in claim 9, wherein the catalyst bodies of the second catalyst zone have, based on the mass of the catalyst bodies, a lower active composition loading than the catalyst bodies of the third catalyst zone.

11. The catalyst arrangement as claimed in claim 9, wherein the catalyst bodies of the second catalyst zone have an active composition having a higher BET surface area than those of the third catalyst zone.

12. The catalyst arrangement as claimed claim 9, wherein the catalyst bodies of the second catalyst zone have an active composition having a higher percentage $V_2O_5$ content, based on the mass of the active composition, than those of the third catalyst zone.

13. The catalyst arrangement as claimed in claim 9, wherein the catalyst bodies of the second catalyst zone have an active composition having a higher promoter content, based on the mass of the active composition, than those of the third catalyst zone.

14. The catalyst arrangement as claimed in claim 1, wherein the length of the first catalyst zone in the gas flow direction is from 5 to 25% of the length of the reactor in the gas flow direction.

15. The catalyst arrangement as claimed in claim 9, wherein the length of the second catalyst zone in the gas flow direction is from 30 to 60% of the length of the reactor in the gas flow direction.

* * * * *